United States Patent
Edwardson et al.

(10) Patent No.: US 6,268,483 B1
(45) Date of Patent: *Jul. 31, 2001

(54) COMPOSITIONS USEFUL AS FIBRIN SEALANTS

(75) Inventors: Peter A. D. Edwardson, Leeds; John E. Fairbrother, Sychdyn; Ronald S. Gardner, Shotton; Derek A. Hollingsbee, Neston; Stewart A. Cederholm-Williams, Oxford, all of (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/094,239

(22) Filed: Jun. 9, 1998

(30) Foreign Application Priority Data

Jun. 9, 1997 (GB) ................................................ 9711927

(51) Int. Cl.$^7$ .................................................... A61K 35/14
(52) U.S. Cl. .......................... 530/382; 530/381; 530/383; 530/384; 424/529; 514/2; 514/8; 514/21
(58) Field of Search ..................... 530/381, 382, 530/383, 384; 435/214; 424/94.64, 529, 530; 514/2, 8, 21

(56) References Cited

U.S. PATENT DOCUMENTS

| | | | | |
|---|---|---|---|---|
| 4,442,655 | * | 4/1984 | Stroetmann | 53/428 |
| 5,206,140 | * | 4/1993 | Marder et al. | 435/7.1 |
| 5,585,007 | * | 12/1996 | Antanavich et al. | 210/782 |
| 5,739,288 | * | 4/1998 | Edwardson et al. | 530/382 |
| 5,750,657 | * | 5/1998 | Edwardson et al. | 530/382 |
| 5,763,410 | * | 6/1998 | Edwardson et al. | 514/21 |
| 5,763,411 | * | 6/1998 | Edwardson et al. | 514/21 |
| 5,770,194 | * | 6/1998 | Edwardson et al. | 424/94.64 |
| 5,773,418 | * | 6/1998 | Edwardson et al. | 514/21 |
| 5,788,662 | * | 8/1998 | Antanavich et al. | 604/6 |
| 5,804,428 | * | 9/1998 | Edwardson et al. | 435/212 |

OTHER PUBLICATIONS

Triantaphyllopoulos, D.C., Fed. Proc., vol. 32/3(I), p. 336, abstract, 1973.*

* cited by examiner

*Primary Examiner*—Jean C. Witz
(74) *Attorney, Agent, or Firm*—Theodore R. Furman, Jr.; John M. Kilcoyne

(57) ABSTRACT

Novel fibrin monomer compositions which are solutions including additional coharvested components, such as prothrombin and Factor XIII, are useful in fibrin sealant applications. Preferably, the compositions are autologous to the patient receiving the sealant and these compositions may also include coharvested plasminogen, Factor X, antithrombin III and/or fibronectin.

6 Claims, No Drawings

COMPOSITIONS USEFUL AS FIBRIN SEALANTS

FIELD OF THE INVENTION

The invention relates to compositions of fibrin monomer and is more particularly concerned with concentrated fibrin monomer solutions containing other blood proteins or components wherein the fibrin monomer and the blood proteins or components are all autologous. Such compositions are useful, for example, as fibrin sealants.

BACKGROUND OF THE INVENTION

U.S. Pat. No. 5,750,657 to Edwardson et al. describes a completely novel method of preparing a fibrin sealant utilizing a fibrin monomer composition. Fibrin monomer, generated by pre-treatment of fibrinogen with a thrombin-like enzyme, is used in a nondynamic state. As it is applied to a patient in need thereof, the nondynamic conditions are reversed so that the monomer can polymerize to form a fibrin polymer which serves as a fibrin sealant.

One concern in applying a fibrin sealant has been fibrinolytic stability. It has been believed that fibrinolytic factors can prematurely break down a sealant clot so that desired effects are not provided. WO 93/05067 to Baxter International describes a sealant composition with greatly reduced plasminogen levels to help ensure better in vivo residence time or stability. The compositions of WO 93/05067 have preferably no more than 10 $\mu$g/ml of plasminogen.

It is also believed that pre-delivery concentrations of fibrin or fibrinogen need to be high for an effective fibrin sealant. For example, Immuno's marketed Tissucol has approximately 70–100 mg/mil of fibrinogen, Behringwerke's Beriplast has approximately 65–115 mg/ml of fibrinogen, Kaketsuken's Bolheal has approximately 80 mg/ml of fibrinogen and the Baxter sealant is believed to contain approximately 100 mg/ml of fibrinogen.

SUMMARY OF THE INVENTION

It has now been found that compositions containing substantial amounts of plasminogen and having relatively lower concentrations of fibrin or fibrinogen compared to the prior art provide useful fibrin sealants at least comparable to the prior art sealants. In accordance with the present invention it has been found that compositions containing from about 10 to about 30 mg/ml of fibrin monomer, about 10–40 $\mu$g/ml of prothrombin and about 100–200 $\mu$g/ml of plasminogen are extremely useful as fibrin sealants. Preferably, such compositions comprise autologous fibrin monomer, prothrombin and plasminogen and may include other autologous components. More preferably such compositions are the result of a process for concentrating a fibrin monomer solution wherein autologous components selected from one or more of plasminogen, prothrornbin, fibronectin, factor XIII, factor X and antithrombin III are coharvested in autologous form with the fibrin monomer.

DETAILED DESCRIPTION OF THE INVENTION

The novel compositions of the present invention have the advantage that they are preferably autologous compositions. As such, use of these compositions, e.g., as fibrin sealants reduces the potential for viral transmission when compared to pooled products. Because the present compositions include a form of fibrin monomer which is temporarily inhibited from polymerizing, e.g., by lowering the pH, they can be applied to a patient to form a sealant/fibrin polymer as set forth in U.S. Pat. No. 5,750,657 without the need for added exogenous thrombin. Upon application, such fibrin monomer can be converted back to a polymerizable form, e.g., by raising the pH back to neutral, so that a fibrin polymer sealant is formed. Although the compositions of the present invention can be prepared by any known/convenient means, it is preferred that methods in accordance with those in U.S. Pat. No. 5,750,657 are employed. Thus, a plasma fraction can be separated from whole blood and the plasma fraction can be treated with a thrombin-like enzyme (which can be thrombin), preferably batroxobin and more preferably in a derivatized form, e.g., biotinylated batroxobin, to form a fibrin I monomer which will immediately polymerize to an acid-soluble polymer. Dissolving the polymer, e.g., in an acid, provides a fibrin monomer solution. The low pH inhibits the fibrin from polymerizing and thus the fibrin monomer is considered nondynamic as referred to in the '657 patent. Such a method of producing a fibrin monomer solution generally provides that other blood factors/components are trapped within, or otherwise absorbed to, the polymer prior to dissolution. Typically, to use the fibrin monomer solution as one component of a fibrin sealant it is coadministered with a material to catalyze the polymerization of the fibrin monomer. For example, a pH 4 fibrin monomer solution can be coapplied with an alkaline buffer, e.g., a pH 10 buffer, to raise the pH of the fibrin monomer thereby creating an environment where the monomer will polymerize to form a fibrin polymer which is the sealant. Preferably, a source of calcium ions can be added. This is described in the '657 patent. Advantageously, when using the present compositions, the coharvested factor XIII and prothrombin, along with the calcium ions, provide that the factor XIII is activated, the prothrombin is converted to thrombin and the factor XIIIa, thrombin and calcium ions provide for the conversion of fibrin I polymer (or monomer) to fibrin II polymer, to crosslinked fibrin II polymer, i.e., a preferred sealant clot.

Thus, preferred compositions of the present invention comprise about 10–30 mg/ml of fibrin monomer (I, II or des BB) in solution with a low pH, i.e., pH 5 or less, buffer. Acetate buffer or any of the buffers set forth in U.S. Pat. No. 5,750,657 or other similar buffers are suitable. These preferred compositions further include 10–40 $\mu$g/ml of prothrombin and have plasminogen between 100 and 200 $\mu$g/ml (which is about 50 to 100% of the plasminogen present in normal plasma). Preferably these three components are autologous and more preferably they have been coharvested with the fibrin monomer. The present compositions may further include 5–100 $\mu$g/ml of activatable Factor XIII, 45–150 $\mu$g/ml of fibronectin, 2.0–7.0 $\mu$g/ml of Factor X and/or 50–200 $\mu$g/ml of antithrombin III.

TABLE 1 below in the Examples provides a comparison of an exemplary composition of this invention to the Tissucol (Immuno) and Beriplast (Behringwerke) compositions discussed above.

The present preferred compositions are part of a convenient, safe fibrin sealant system in that they are autologous and can be prepared to inherently contain other important factors, i.e., other than the fibrin itself, which provides for the desired conversion and crosslinkage of the fibrin I monomer to a crosslinked fibrin II polymer. Individual extraction and purification of components are necessary with prior art sealant products since they are pooled products. Coharvesting fibrin monomer and other blood components which are naturally carried through in the polymerization/solubilization preparation method described above is a simple way of providing extremely efficient sealant products with enhanced safety and which perform at least comparable to Beriplast and Tissucol. Also, when the novel compositions of the present invention are coapplied to a surgical site with an agent to render the fibrin monomer polymerizable (preferably pH 10 buffer solution; about 7:1 fibrin monomer solution: buffer) and a source of calcium ions, the resulting sealants have stability comparable to prior art sealant without the need for added antifibrinolytic stabilizers, i.e., aprotinin and/or without the need to remove plasminogen.

Using the process described below, compositions of the present invention can be prepared. Preferably, the process is carried out in devices such as those described in EP 654669, WO 96/16715, WO 96/16713 and WO 96/16714.

EXAMPLE 1

120 cc of the patient's blood is drawn and mixed with 17 cc of 4% trisodium citrate USP for anticoagulation. Centrifugation results in the isolation of about 60 cc of plasma which is reacted, i.e., by mild agitation, with biotin-batroxobin for 10 minutes at 37° C. The biotin-batroxobin catalyzes the release of fibrinopeptide A only from fibrinogen and does not activate factor XIII. This results in the formation of a fibrin I polymer which is acid soluble. The fibrin I polymer is isolated by centrifugation and dissolved in 3.5 ml 0.2M sodium acetate buffer (pH 4) in the presence of calcium ions. Avidin covalently bound to agarose is added to the solution which chemically binds the biotin-batroxobin, and the biotin-batroxobin:avidin-agarose complex is then separated from the fibrin I polymer solution by filtration. The resulting fibrin monomer solution has the composition shown in TABLE 1.

EXAMPLES 2–24

Twenty-three additional blood samples were processed as in Example 1 and the resulting compositions were analyzed. The results are compiled to show the ranges as set forth in Table 1. Table 1 also shows the plasma levels of each component in the 24 subjects tested and further compares the present formulations to those of the Tissucol (Immuno), Beriplast (Behringwerke) and Bolheal (Kaketsuken) sealants.

TABLE 1

| | Fibrin Monomer Compositions | | | | | |
|---|---|---|---|---|---|---|
| | Example 1 | Range EX 1– EX 24 | Plasma EX 24 | Tissucol | Beriplast | Bolheal |
| Fibrin (ogen) mg/ml | 19 | 16.6– 24.5 | 1.68– 3.56 | 70–110 | 64–115 | 80 |
| Prothrombin μg/ml | 24 | 15.36– 32.0 | 58.96– 99.8 | — | — | — |
| Fibronectin μg/ml | 127 | 48.6– 140 | 123.6– 597.1 | 2–9 (mg/ml) | 3–7 (mg/ml) | — |
| Plasminogen μg/ml | 140 | 114– 234 | 137– 324 | — | — | — |
| Factor XIII μg/ml (Units) | 30 (1.43) | 14– 100.8 (.7–5) | 10–30.7 (0.5– 1.45) | — (10–50) | — (60) | — (75) |
| Antithrombin III μg/ml | 90 | 58–162 | 161– 323 | — | — | — |
| Factor X | 3.1 | 2.1–4.9 | 7.48– 13.8 | — | — | — |

What is claimed is:

1. A method of forming a fibrin polymer for medical use on or in a patient comprising the steps of taking a blood sample from said patient;

harvesting a solution from said blood sample which comprises 10–30 mg/ml of non-dynamic fibrin monomer, 10–40 μg/ml of prothrombin and 5–100 μg/ml of Factor XIII; and forming said fibrin polymer for use on or in said same patient.

2. The method of claim 1 wherein said solution further comprises 100–200 μg/ml of plasminogen.

3. The method of claim 1 wherein said solution further comprises 45–150 μg/ml of fibronectin.

4. The method of claim 1 wherein said solution further comprises 2.0–7.0 μg/ml of Factor X.

5. The method of claim 1 wherein said solution further comprises 50–200 μg/ml of antithrombin III.

6. The method of claim 1 wherein said solution is harvested by the steps of (a) separating a plasma fraction from said blood sample;

(b) treating the plasma fraction with an enzyme which catalyzes the cleavage of fibrinopeptides A and/or B from fibrinogen within said plasma to form a fibrin polymer;

(c) substantially removing all of the remaining plasma from the so-formed polymer; and (d) dissolving the polymer to provide a fibrin monomer solution containing said co-harvested autologous components.

* * * * *